United States Patent [19]

Nichols

[11] Patent Number: 5,067,944
[45] Date of Patent: Nov. 26, 1991

[54] HYPODERMIC NEEDLE GUARD

[75] Inventor: Robert N. Nichols, Lakewood, Ohio

[73] Assignee: Jerry Robles, Oracle, Ariz.

[21] Appl. No.: 481,782

[22] Filed: Feb. 16, 1990

Related U.S. Application Data

[63] Continuation of Ser. No. 215,298, Jul. 5, 1988, abandoned.

[51] Int. Cl.$^5$ .................. A61M 5/32; B65D 83/10
[52] U.S. Cl. .................. 604/192; 604/263; 206/365
[58] Field of Search ............ 604/192, 197, 263, 110; 206/365, 366; 128/763-765

[56] References Cited

U.S. PATENT DOCUMENTS

| | | | |
|---|---|---|---|
| 3,055,364 | 9/1962 | Myerson et al. | 206/365 |
| 3,074,542 | 1/1963 | Myerson et al. | 206/365 |
| 3,439,675 | 4/1969 | Cohen | 604/192 |
| 4,573,975 | 3/1986 | Frist et al. | 604/192 |
| 4,623,336 | 11/1986 | Pedicano et al. | 604/192 |
| 4,742,910 | 5/1988 | Staebler | 604/192 |
| 4,767,412 | 8/1988 | Hymanson | 604/192 |
| 4,781,697 | 11/1988 | Slaughter | 604/263 |
| 4,840,618 | 6/1989 | Marvel et al. | 604/187 |
| 4,850,976 | 7/1989 | Heinrich et al. | 604/192 |
| 4,880,413 | 11/1989 | Giuffre et al. | 604/192 |
| 4,892,522 | 1/1990 | Suzuki et al. | 604/192 |
| 4,892,525 | 1/1990 | Hermann et al. | 604/263 |
| 4,919,656 | 4/1990 | Bracker et al. | 604/192 |
| 4,928,824 | 5/1990 | Barasch | 206/365 |

FOREIGN PATENT DOCUMENTS

| | | | |
|---|---|---|---|
| 3433359 | 4/1986 | Fed. Rep. of Germany | 604/192 |
| 2586566 | 3/1987 | France | 604/192 |

Primary Examiner—C. Fred Rosenbaum
Assistant Examiner—Mark O. Polutta
Attorney, Agent, or Firm—Oldham & Oldham Co.

[57] ABSTRACT

A hypodermic needle guard designed to avoid needle sticks comprising a hand shield in the form of a flat plate with a flexible, tubular needle cap holder connected about a hole in the plate's center. Needle cap-enclosed hypodermic needles attached to medical appliances such as syringes, are inserted through the hole into the holder, where the user grasps the cap through the holder tube by compressing the tube with finger pressure. The needle attached to the appliance is then withdrawn. The process is reversed to safely recap the hyperdermic needle.

9 Claims, 1 Drawing Sheet

HYPODERMIC NEEDLE GUARD

This is a continuation of copending application Ser. No. 07/215,298 filed on July 5, 1988, abandoned.

TECHNICAL FIELD

This invention relates to a safety device for protecting individuals against puncture wounds caused by accidents with hypodermic needles. More particularly, this invention relates to a method for safely capping and uncapping hypodermic needles, for example, those attached to a hypodermic syringe. Specifically, this invention relates to a hand-held hypodermic needle guard that includes a shield plate with a flexible needle cap holder tube attached thereto into which caps covering hypodermic needles can be inserted and grasped by compressing the tube with the fingers of the shield holding hand, thus allowing the hypodermic needle to be withdrawn from, or reinserted into the cap without risk of inadvertent contact of the needle with the holding hand.

BACKGROUND OF THE INVENTION

Hypodermic needles are widely used throughout the medical community, and elsewhere, to administer medication and nutrients, for drawing blood samples, and for numerous other purposes. The use of such devices is not without risk, however, and while the Center for Disease Control in one study of needle stick injuries from hypodermic needles incurred by phlebotomists showed only one occurrence in over three thousand needle procedures, the consequence of a needle stick can be severe, and sometimes fatal.

As is widely known, the human immunodeficiency virus, HIV, can be readily transmitted through the use of contaminated needles, and while the risk of HIV transmission from a contaminated needle stick is less than 1%, according to the Center, the results are often fatal. Further, the risk of transmission of the more common hepatitis B virus is much greater, and incidents of needle stick have also been implicated in connection with the transmission of the various herpes viruses, malaria, rocky mountain spotted fever, and tuberculosis.

While inadvertent needle sticks can also happen during the insertion or removal of needles from patients, in one study, recapping and disposal of hypodermic needles accounted for over half of such occurrences.

The problem and consequences of needle sticks have long been recognized as serious, and considerable attention has recently been directed to the problem. For example, procedures calling for elimination of the recapping of needles and deliberately breaking them to prevent their falling into the hands of illegal users, as well as similar expedients designed to reduce the risk of needle sticks have been suggested. Such procedures have frequently been either deliberately, or carelessly disregarded, however, and needle stick accidents have, unfortunately, continued at unacceptable rates.

Needle guard protective devices have also been proposed to reduce the problem, including one such device having a central hole in a finger-protecting shield that allows a needle cap to be inserted therethrough, and grasped prior to recapping. One problem associated with the device, however, arises from the fact that its use is necessarily restricted to needle caps having a diameter corresponding to the hole in the shield. Consequently, the device cannot be used with the wide variety of needle caps commonly encountered by the medical profession. Other devices have also been proposed which allow the needles attached thereto to be protectively withdrawn into the device following use. Such devices, however, fail to respond to the need to protect the standard hypodermic syringes already in use, and it may confidently be assumed that the complexity of the devices, and their cost will never allow them to entirely replace the untold numbers of standard hypodermic syringes in use today.

Furthermore, while injury prevention training is helpful in avoiding needle stick accidents, studies have indicated that education is relatively short lived, and that behavioral changes are the least effective method of preventing such accidents.

Other approaches, including cut-resistant gloves; reusable, gas-powered, needle-free injectors, and various other techniques and equipment have also been suggested, but until the discovery of the invention described herein, a simple, cost-effective way in which to avoid needle stick injuries has been unavailable.

DISCLOSURE OF THE INVENTION

In view of the preceding, therefore, it is a first aspect of this invention to provide protection to medical workers, and others, from diseases contractible as the result of accidental penetration of the skin by a contaminated, hypodermic syringe needle.

A second aspect of the invention is to provide a compact, portable safety device designed to avoid the spread of contagious disease caused by involuntary, self-inflicted wounds from septic hypodermic needles.

Another aspect of this invention is to provide an inexpensive, easy-to-use device for protection against accidental hypodermic needle sticks.

A further aspect of this invention is to provide a hypodermic syringe needle guard that requires no special training to use.

An additional aspect of this invention is to provide a safe way to uncap and recap hypodermic needles.

Still another aspect of the invention is to provide a device which shields a user's hands from inadvertent needle puncture wounds of the type commonly resulting from the operation of hypodermic syringes.

In light of the foregoing, therefore, the above and other aspects of the invention, which are disclosed in the following detailed description of the invention, are obtained by a medical protection device comprising a hand shield with a hypodermic needle cap holder tube connected thereto, said hand shield comprising a flat plate with a hole suitable for the insertion of a needle cap substantially in the center thereof, and said needle cap holder tube comprising a flexible, cylindrical tube having an open end therein connected about said hole at right angles to said plate, and having a closed end therein opposite to said open end, said tube being compressible about its transverse axis through the application of finger pressure by a user.

The foregoing and still other aspects of the invention are obtained by the process of capping a hypodermic needle comprising inserting said needle into a needle cap contained in the needle cap holder tube of the device of claim 1, said needle cap being firmly held within said holder by compressing said holder tube against said needle cap with finger pressure.

BRIEF DESCRIPTION OF THE DRAWINGS

The invention will be better understood when reference is had to the following drawings, in which like numbers refer to like parts, and in which.

DETAILED DESCRIPTION OF THE INVENTION

Figure 1:
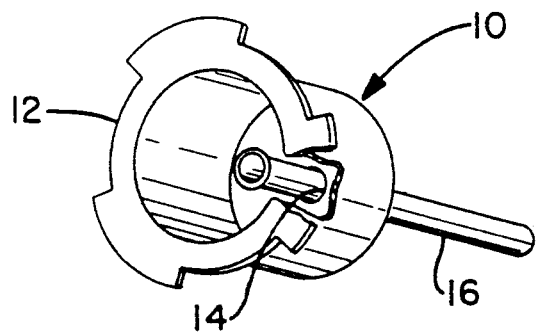
FIG. 1 is an isometric view of a prior art device with a needle cap inserted therein.

FIG. 1 shows an isometric view of a prior art device, generally 10, consisting of a finger shield 12, containing a needle cap insertion hole 14 showing a needle protector or cap 16 in the form of a protective, closed-end tube is inserted therethrough. In use, the finger shield is held in one hand, while the other hand pushes a hypodermic needle contained in a needle cap through hole 14. The lower portion of the needle cap is then grasped with the fingers of the first mentioned hand, and the hypodermic needle fitted implement, for example a hypodermic syringe, is withdrawn. After the hypodermic needle has been used, the procedure is reversed, that is, the hypodermic needle is reintroduced into the needle cap 16, and the latter is withdrawn from the insertion hole 14. While the device described has been credited with substantially reducing needle stick injuries, it has some inherent disadvantages. One of these, for example, stems from the fact that the insertion hole 14 is designed for a needle cap having a particular diameter; a larger cap will not fit through the hole, while a smaller one leaves an annular space between it and the finger shield, exposing the user to penetration of the hypodermic needle through the space, and to a resulting needle stick. In addition, while the finger shield protects the fingers, a considerable area of the hand is left exposed to inadvertent contact with the hypodermic needle.

Figure 2:
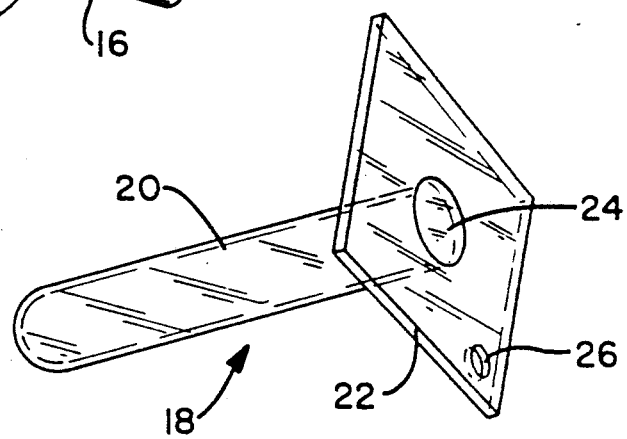
FIG. 2 is an isometric view of the hypodermic needle guard device of the invention.

FIG. 2 is an isometric view of the hypodermic needle guard device of the invention, generally 18, comprising a hand shield 22 connected to a flexible needle cap holder tube 20. The hand shield 22 contains a needle cap insertion hole 24, and optionally, an attachment hole 26 which allows the device to be readily fastened to the person of a user, for instance by means of a key chain, so that the device will always be readily available for use.

The hypodermic syringe needle guard 18 is used by inserting the needle cap enclosed hypodermic needle through the insertion hole 24 into the interior of the flexible needle cap holder tube 20 which is held in one hand of the user. When the needle cap has been thus inserted, the user squeezes the needle cap through the needle cap holder tube, compressing it about, and immobilizing the needle cap. The hypodermic needle is then safely withdrawn for use. To recap the hypodermic needle, the procedure is reversed, that is, the needle cap is held within the cap holder tube 20 by applying finger pressure to compress the flexible needle cap holder tube, and the hypodermic needle is reinserted into the needle cap. The user's finger pressure is then released, and the cap enclosed hypodermic needle is withdrawn from the needle guard 18 for disposal. Some procedures then call for carrying the protected hypodermic needle to a disposal area where the hypodermic needle and protective needle cap are detached from the syringe or other apparatus with which they are associated and dropped as a unit into a disposal container. Other procedures simply direct that the entire apparatus, for example, a plastic syringe, together with an attached cap-protected hypodermic needle be placed in the disposal container.

The shape of the shield 22 may be varied; however, it has been found convenient to fabricate it as a square flat plate, large enough to substantially cover the hand holding it. A flat sided shield, such as the square shaped shield illustrated in FIG. 2 is preferred, since it will not move, for instance roll, when placed on a flat surface.

The hand shield 22 may be made from any of a variety of materials, for example, it may be fabricated from metal, plastic, rubber, and similiar materials. Plastic materials are preferred however, such as PVC, polystyrene, acrylics, and the like. As may be inferred from the materials mentioned, the hand shield may be opaque; however, the use of translucent, or transparent materials are preferred, especially transparent materials, since they make the user more aware of the position of the hand holding the needle guard, and therefore, assist in coordinating the movement of the hypodermic needle relative to the holding hand, helping to avoid accidental contact between the two. The flexible needle cap holder tube 20 may be selected from any suitable flexible material including the polyolefins, for example, polypropylene, polyethylene and the like, as well as flexible PVC, rubber, and similar materials. PVC, particularly plastisol PVC resins, have been found to be particularly useful in the application, however, since they can be readily dip-molded to form the cap holder tube. As in the case of the hand shield, the use of translucent, more preferably, transparent materials is desirable, since they enable observation of a needle cap's location within the cap holder tube, facilitating application of finger pressure at the proper point. In a preferred embodiment, the use of a transparent acrylate for the hand shield member, and a substantially transparent PVC plastisol resin for fabricating the flexible needle cap holder tube are employed. Such a combination may be readily cold sterilized with antiseptic solutions, where sterilization is desired.

Figure 3:
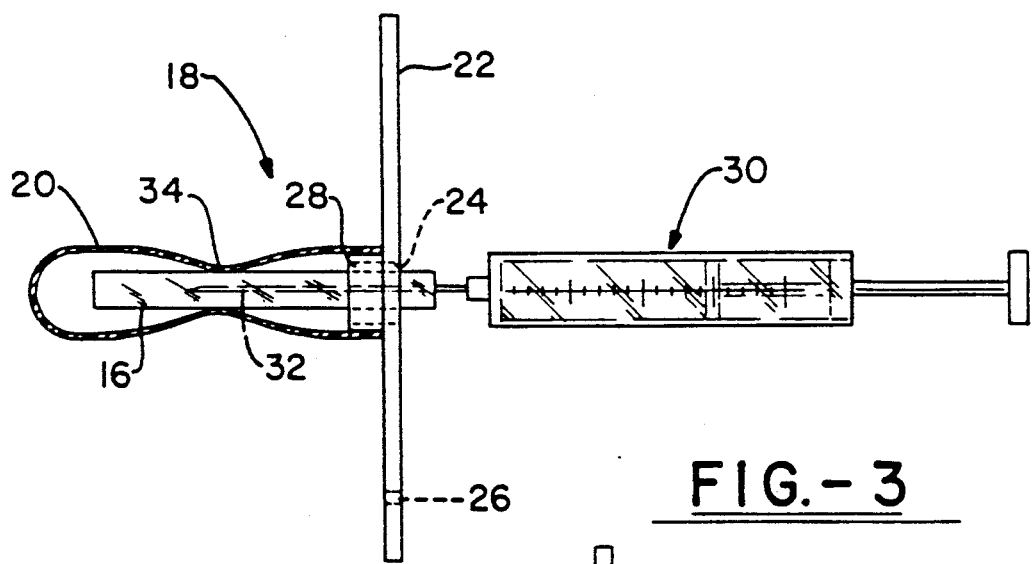
FIG. 3 is a side elevation of the hypodermic needle guard device of the invention with a capped hypodermic needle attached to a hypodermic syringe inserted therein.

FIG. 3 is a side elevation of a transparent hypodermic needle guard device of the invention showing a capped needle attached to a hypodermic syringe, generally 30, inserted therein. In the Figure the flexible needle cap holder tube 20 is fastened to the hand shield 22 by means of a connector collar 28, formed as a unitary part of the shield. Instead of the unitary collar shown, other means of connection might also be used, however, for example, the male portion of a two-component grommet fitting, or a flange formed on the open end of the holder tube 20 fastened to the underside of the hand guard 22 by an adhesive, or by other means. In the case of the collar shown, or where a male grommet component is employed, the open end of the needle cap holder tube can be held firmly in place over the collar, or the male portion of the grommet, as the case may be, by means of a force fit, or optionally, the connection may be strengthened even more with an adhesive. In any event, the needle cap enclosed hypodermic needle 32 is inserted through the insertion hole 24 in hand guard 22, into the interior of the flexible needle cap holder tube 20, and pressure is applied, for instance at compressed area 34, to hold the needle cap 16 firmly in place. Hypodermic needle 32 is then removed, or reinserted, as previously described.

The dimensions of the hypodermic needle guard device may be varied within fairly broad limits. For example, the hand shield can have sides ranging from about two inches to four inches long, in the case of square hand guards, and can be anywhere from about one-eighth to one-quarter inch thick. Although possible, smaller sides increase the risk of needle stick, while larger sides tend to be too bulky to handle conveniently. Similarly, while also possible, thinner guards suffer from being too fragile, while thicker ones inconveniently increase the weight of the device.

The diameter of the insertion opening 24 may also vary widely, however, it should be sufficiently large to accommodate the diameters of the more commonly used needle caps. In this connection, it has been found that an opening of from about one-quarter inch to one-half inch provides a satisfactory opening for the majority of needle caps, and it is, therefore, preferred that the opening diameter be within such range. The needle cap holder tube should be long enough to accept needle caps in ordinary use, which typically range from about one and one-half inch to four inches long; consequently, it is desirable that the length of the needle cap holder tube used be at least about four inches long. The wall thickness of the needle cap holder tube should also be thick enough to resist needle penetration, and in this regard in the case of the flexible PVC holders referred to, it has been found that the wall thickness may conveniently range from about 0.04 inch to 0.06 inch.

Figure 3A:
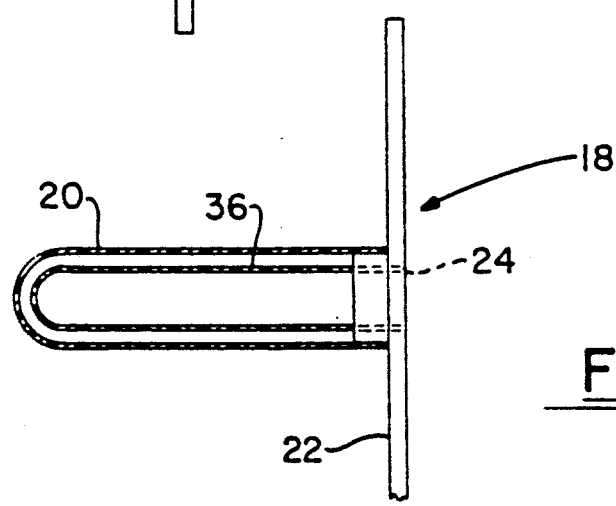
FIG. 3A shows a side elevation of the hypodermic needle guard device of FIG. 3 with a size-modification sleeve inserted therein.

FIG. 3A shows a side elevation of the hypodermic needleguard device 18 of FIG. 3 with a size-modification sleeve 36 inserted therein. In some instances, as for example, in the case of subcutaneous injections, smaller needles are employed than in the case of needles used for intramuscular or intravenous procedures. In such instances, it is sometimes of advantage to provide a needle cap holder tube having a reduced diameter, since the needle caps associated with the smaller needles normally also have smaller diameters. Although not essential, a needle cap holder tube having a smaller diameter allows the smaller needle caps to be grasped much more firmly, and the use of a size-modification insert sleeve in such cases is, therefore, preferred. In this connection, it has been found that the use of a flexible size-modification insert sleeve 36, fabricated in essentially the same way as the needle cap holder tube 20, but smaller than the latter, is ideally suited for use with the smaller needles and needle caps. As shown in the Figure, the sleeve 36 is simply introduced through the insertion hole 24 of hand shield 22, where it is retained by virtue of a frictional fit within the hole. When its use is no longer required, it may conveniently be removed by simply pinching the end of the needle cap holder tube 20, thereby forcing the sleeve far enough out of insertion hole 24 to be grasped and removed.

While in accordance with patent statutes, the preferred embodiment and best mode has been presented, the scope of the invention is not limited thereto, but rather is measured by the scope of the attached claims.

What is claimed is:

1. A medical protection device comprising a hand shield with a hypodermic needle cap holder tube connected thereto, said hand shield comprising a flat plate with a hole suitable for the insertion of a needle cap substantially in the center thereof, and said needle cap holder tube comprising a transparent flexible, cylindrical tube having a wall thickness of between 0.04 to 0.06 inches and an open end therein connected about said hole at right angles to said plate, and having a closed end therein opposite to said open end, said tube being compressible about its transverse axis through the application of pinching finger pressure by a user.

2. A device according to claim 1 wherein said plate is formed with a cylindrical collar as an integral part thereof, said collar being concentric to, and extending at right angles from said hole, and wherein the open end of said tube makes a force fit over said collar, thereby effecting a connection between said tube and said plate.

3. A device according to claim 1 in which said plate and said tube are formed from substantially transparent plastic materials.

4. A device according to claim 3 in which said plate is square, having sides of from about two inches to three-and-one-half inches long.

5. The process of capping a hypodermic needle comprising inserting said needle into a needle cap contained in the needle cap holder tube of the device of claim 1, said needle cap being firmly held within said holder by compressing said holder tube against said needle cap with finger pressure.

6. A device for protecting the hands of a user of a needle for injecting or extracting body fluids having a needle sheath from accidental needle sticks while unsheathing or resheathing said needle, said device comprising:
   a hand shield, said hand shield comprising a flat plate with an unobstructed hole therethrough positioned substantially in the center of said plate;
   a transparent flexible cylindrical tube having a wall thickness of between 0.04 to 0.06 inches and one open end therein, said tube being sufficiently flexible about its transverse axis to be compressed by pinching finger pressure of the user to grasp a needle sheath placed therein; and
   a means for connecting said open end of said tube about said hole at a right angle to said plate.

7. The device of claim 6 wherein the means for connecting comprises a cylindrical collar formed integral to said plate, said collar being concentric to, and extending at right angles from, said hole, and said collar being sized to frictionally engage the inner surface of the open end of said tube, thereby effecting connection between said plate and said tube.

8. The device of claim 6 wherein said plate and said tube are formed from substantially transparent plastic materials.

9. The device of claim 6 wherein the plate is square, having sides of from about two inches to about three-and-one-half inches.

* * * * *